United States Patent [19]

Camp et al.

[11] Patent Number: 5,734,115
[45] Date of Patent: Mar. 31, 1998

[54] ACCELERATED FADE APPARATUS AND METHOD OF ITS USE

[75] Inventors: Alphonse D. Camp; Keith B. Kahen, both of Rochester; Gary A. Granath, Fairport; Gerald W. Smith, Churchville, all of N.Y.

[73] Assignee: Eastman Kodak Company, Rochester, N.Y.

[21] Appl. No.: 763,634

[22] Filed: Dec. 4, 1996

[51] Int. Cl.⁶ .................................................. G01N 25/00
[52] U.S. Cl. ..................................... 73/365.6; 73/159
[58] Field of Search ........................ 73/159, 865.6; 362/1, 2

[56] References Cited

U.S. PATENT DOCUMENTS

| | | |
|---|---|---|
| 3,576,125 | 4/1971 | Kockott et al. |
| 3,797,918 | 3/1974 | Kockott .................... 362/2 |
| 4,544,995 | 10/1985 | Suga . |
| 4,627,287 | 12/1986 | Suga . |
| 4,704,903 | 11/1987 | Suga et al. |
| 4,760,748 | 8/1988 | Katayanagi et al. |
| 4,843,893 | 7/1989 | Huber et al. ............ 73/865.6 |
| 4,995,273 | 2/1991 | Kisima et al. ........... 73/865.6 |
| 5,138,892 | 8/1992 | Suga . |

FOREIGN PATENT DOCUMENTS 404340441  11/1992  Japan ........................ 73/865.6

OTHER PUBLICATIONS

Derwent Abstract DE 4330759, Mar. 1995.
Derwent Abstract JP 7234181, Sep. 1995.

Primary Examiner—Robert Raevis
Attorney, Agent, or Firm—Paul A. Leipold

[57] ABSTRACT

The invention relates to an apparatus for light fastness testing comprising a light source, means for dividing ultraviolet and visible light from infrared rays, means to direct the visible component of light into spherical cavity, and means to mount test samples in apertures in said cavity.

24 Claims, 3 Drawing Sheets

ACCELERATED FADE APPARATUS AND METHOD OF ITS USE

FIELD OF THE INVENTION

This invention relates to apparatus for testing material for light fastness and deterioration under light. It particularly relates to a machine and method for testing of photographic materials.

BACKGROUND OF THE INVENTION

The testing of photographic materials for stability to light is carried out in order to predict the behaviors of such materials years in the future. Generally these tests are accelerated by applying relatively high levels of light to the materials for periods of between 3 weeks and 6 months, sometimes under elevated temperature conditions. The testing devices generally provide about 50K lux light. The typical device has a group of stationary light sources or a single 360° light source located inside a generally spherical arrangement. The samples are attached to the inside of the spherical framework, and the framework is rotated around the light source.

In another type of device, the light is in a box, and samples are arranged at various distances from the light source in order to obtain the exposure over a time period. In the box arrangement, the humidity and temperature also may be controlled to provide further accelerated aging effects or to simulate the use of the photograph in high exposure conditions.

Devices for testing light fastness also have been utilized in the paint and dye industry. Some such devices are merely arrangements of materials in areas such as Florida where there is a high percentage of sunlight available.

The previous devices suffered from several disadvantages. The long exposure periods required of 3 weeks to 6 months required research projects involving a need to know of stability improvements to proceed very slowly. Further, the light sources would vary in intensity over the term of the test as bulbs were replaced or aged so the test device puts out a different amount and quality of light. In addition, it was often difficult to control humidity and temperature conditions during the 6-month test, as the seasonal changes in the typical office or laboratory building occurred.

U.S. Pat. No. 5,138,892—Suga discloses a test device with the central light source with samples rotating around the source. U.S. Pat. No. 4,704,903—Suga et al discloses a light fastness testing machine with air flow control. U.S. Pat. No. 4,544,995—Suga discloses a light fastness testing machine with humidity control. U.S. Pat. No. 4,760,748—Katayanagi et al discloses a testing device with rotation of samples around a central light source.

PROBLEM TO BE SOLVED BY THE INVENTION

There is a need for a device to accurately, repeatably, and rapidly subject photographic materials to accelerated light fastness testing.

SUMMARY OF THE INVENTION

It is an object of the invention to overcome difficulties in color stability testing of prior apparatus and methods.

It is another object of the invention to provide a reliable light stability data in about two days.

It is another object of the invention to provide repeatable light stability data.

It is another object of the invention to provide a means to understand reciprocity law in failure of accelerated fade. The device has been shown to operate from 50K lux to 700K lux.

These and other objects of the invention generally are provided by providing apparatus for light fastness testing comprising a light source, means for dividing visible light from ultraviolet infrared radiation, means to direct the visible component of light into a spherical cavity, and means to mount test samples in apertures in said cavity.

In another embodiment the invention provides a method of light fading comprising providing apparatus for light fastness testing comprising a light source, a splitter for dividing visible light from infrared rays, means to direct the visible component of light into spherical cavity, and means to mount test samples in apertures in said cavity, placing test samples in said apertures, and subjecting said samples to light levels of greater than 500,000 Lux.

ADVANTAGEOUS EFFECT OF THE INVENTION

The invention provides the advantage that light stability testing of photographic materials may be carried out rapidly. The invention further provides a method and apparatus of light testing that is repeatable. The method and apparatus of the invention further provide the advantage that the testing has temperature stability, as well as completion of testing to allow prediction of many years of fade based on a test lasting less than three weeks.

DETAILED DESCRIPTION OF THE INVENTION

The invention has numerous advantages over prior apparatus and process. The invention allows the rapid testing of samples under very uniform and repeatable conditions. Further, the invention allows very high exposure to light in 10 to 20 days to surprisingly allow prediction of 20-year stability as accurately as the present 6-month low intensity test. The device further is compact and reliable. The device allows the samples themselves to have their temperature controlled independently from the amount of light to which they are exposed. The device further allows uniform exposure of all samples being tested at the same time. Present devices have a variance between exposure of samples in the middle of the collection as opposed to samples at the edges. The apparatus of the invention further allows repeatable results with different apparatus rather than having tests of stability only comparable between samples tested in the same apparatus. These and other advantages will be apparent from the discussion below.

Figure 1:
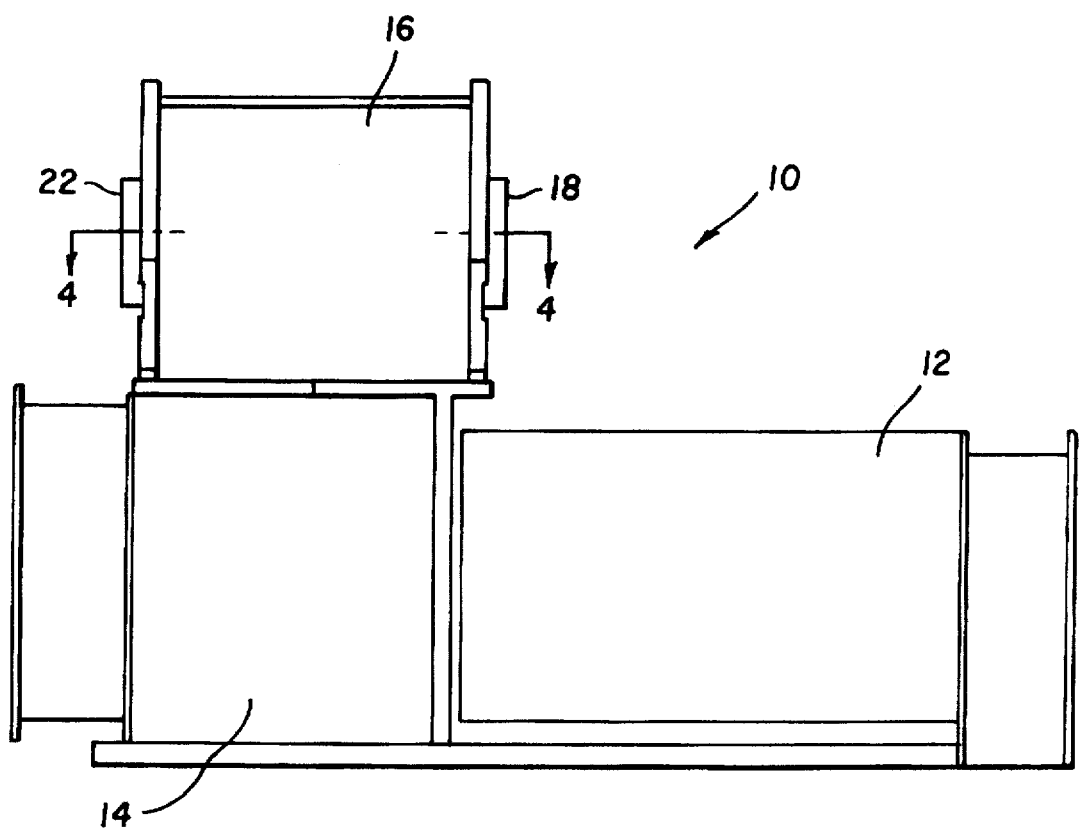
FIG. 1 is a side view of a schematic of the apparatus of the invention.
Figure 2:
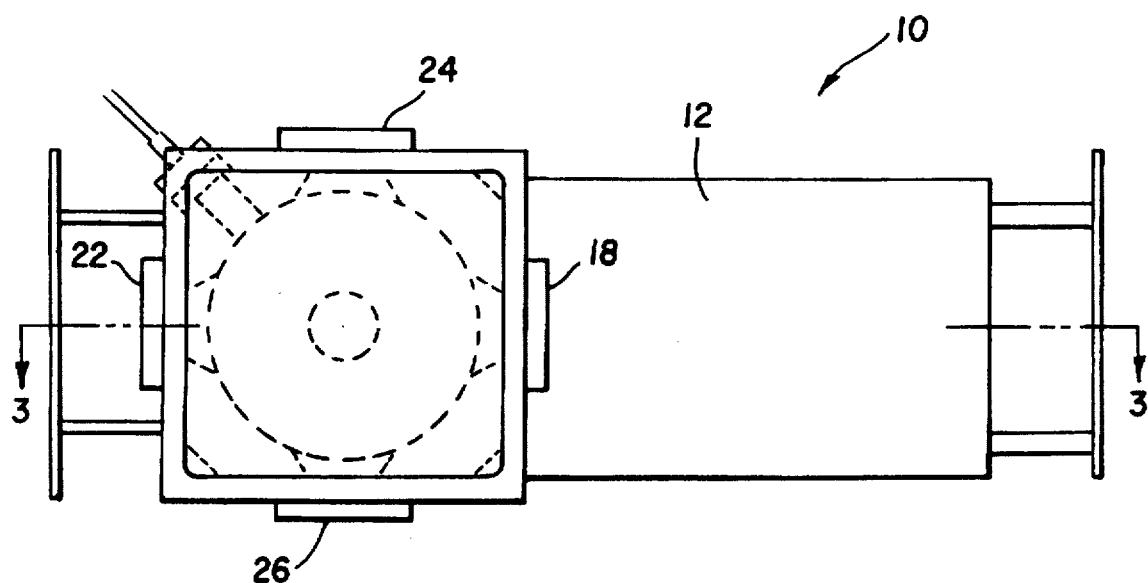
FIG. 2 is a top view of the apparatus of the invention.

FIG. 1 is a schematic illustration of the apparatus of the invention 10 from a side view. The device is enclosed by covers 12 over the light source 14 over the mirror and light splitter and covers over the fade chamber itself. FIG. 2 is a top view of the apparatus 10. In FIGS. 1 and 2, holders 18, 22, 24, and 26 are for samples to be tested.

Figure 3:
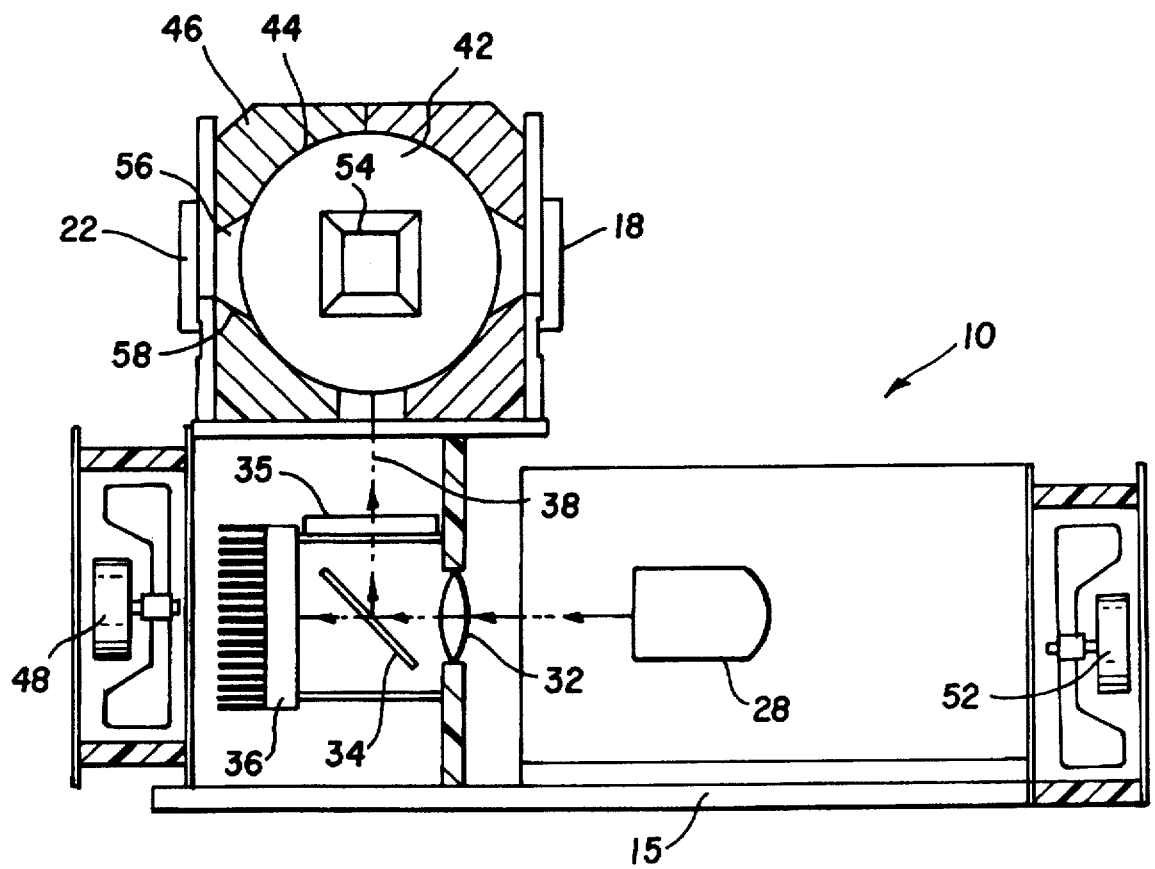
FIG. 3 is a side view on cross-sectional line 33 of FIG. 2 of the apparatus of the invention.

In the cross-sectional view of FIG. 3 taken on line 3—3 of FIG. 2, there is schematically shown a light source 28. Source 28 provides a beam of light that passes through the beam collimating lens 32. This provides a collimated source that is focused onto the cold mirror 34 splitter that allows the passage of unwanted radiation such as infrared rays and UV radiation to heat sink 36. The light 38 reflected by cold mirror splitter 34 and then passes through a heat absorber 35 before it enters chamber 42 that has an angular interior wall 44 and is formed from material 46 that is generally a white reflective material. The apparatus 10 is provided with fan 48 and 52 which both direct air out of the device to cool the lamp and the heat sink. Further, air is directed downward into the chamber 42 in order to provide cooling air past the samples held by sample holders 18, 22, 24, and 26. The opening 54 has been beveled so as to prevent shadow areas on the sample exposed in opening 54. The beveled edge 58 of opening 56 better shows the cross section of the opening allowing uniform exposure onto the test sample. Apparatus 10, includes a base 15 that supports the apparatus 10. While any known sample holder may be utilized, a preferred sample holder is disclosed in copending coassigned patent application U.S. Ser. No. 08/760,432, of Camp et al filed simultaneously with this application.

Figure 4:
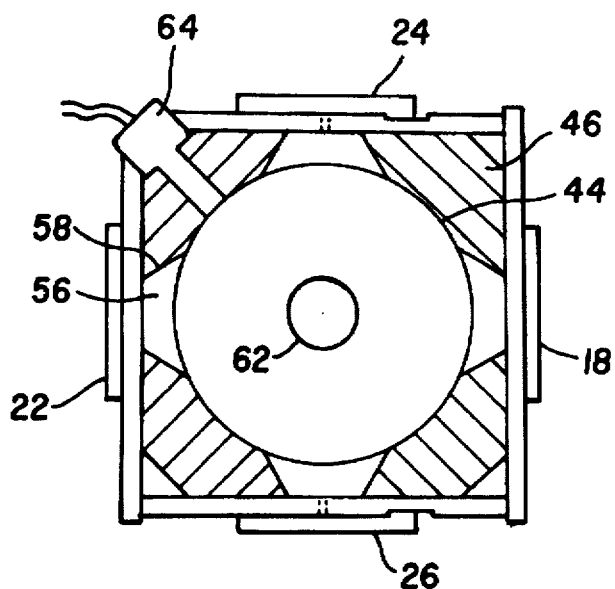
FIG. 4 is a cross-sectional view on line 4—4 of FIG. 1 of the apparatus of the invention.

FIG. 4 is a cross-sectional view of the chamber on line 4—4 of FIG. 1 looking downward towards the inlet opening 62 where light enters the chamber 44. The chamber is provided with a sensing device 64 that reads the intensity of light being applied to the surface of the chamber 44. This allows the intensity of the lamp to be adjusted to maintain the uniform and exact exposure at all times on the samples.

The lamp utilized in the testing device of the invention may be any suitable lamp that provides a strong enough light source. A preferred lamp has been found to be an Xenon illuminator incorporating reflector and having a wattage of at least 500 watts. Such a lamp results in a light intensity in the chamber of between 500 and 600K lux by providing the Xenon source external to the sample chamber 44. There allows a uniform of exposure to light and generating less heat as the heat generating portion of the beam is removed by the cold mirror and heat absorber. The mirror which reflects test light up into the chamber while allowing splitting of the IR and UV portions which generate heat is formed of any material that will pass these kinds of radiation while reflecting light. A preferred material has been found to be a cold mirror. In addition a heat absorber is used to minimize IR.

The fans that provide cooling air or flow are selected such that they are able to remove heat from the system While providing air flow throughout the device including down through the chamber.

The chamber itself has a white interior such that light will be reflected numerous times within the chamber resulting in uniform exposure to the samples in the four windows. The material forming the chamber may be any desirable material; however, a white thermoplastic resin known as Spectrolon has been found to be suitable, as it is chemically inert and stable. Further, it provides a surface that is white. It is anticipated that other materials could be utilized that are white or have been coated with a white surface. The annular interior surface of the chamber provides a spherical area of any desired size allowing uniform exposure at a high level. Generally it has been found that a size of between 5 and 15 inches in diameter is suitable. A preferred diameter has been found to be about 6 inches for the Xenon illuminator of about 500 watts.

The control system comprising the sensor 64 and regulating device, not shown, to control the lamp to provide uniform power and response to the sensor may consist of operational integrator circuit.

As pointed out, the ports of the sphere where the samples are placed have been angled to remove any shadowing due to the sphere wall's thickness. It has Generally been found that a 40-degree angle adjacent the port openings will remove any shadows.

The exit holes where the samples are placed generally are of the size of about 1½" square. In this space, several samples may be placed if desired. The sample temperatures are controlled by constant bathing of the sample with high velocity air from the fan 48. Further, the sample holders may also be temperature-controlled by air or liquid flow in the holder. Further, they may be formed out of heat sink material which also would tend to minimize temperature variation. The sample holders also may be provided with thermostats which would allow control of the temperature in response to the sensed temperature of the samples.

Figure 5:
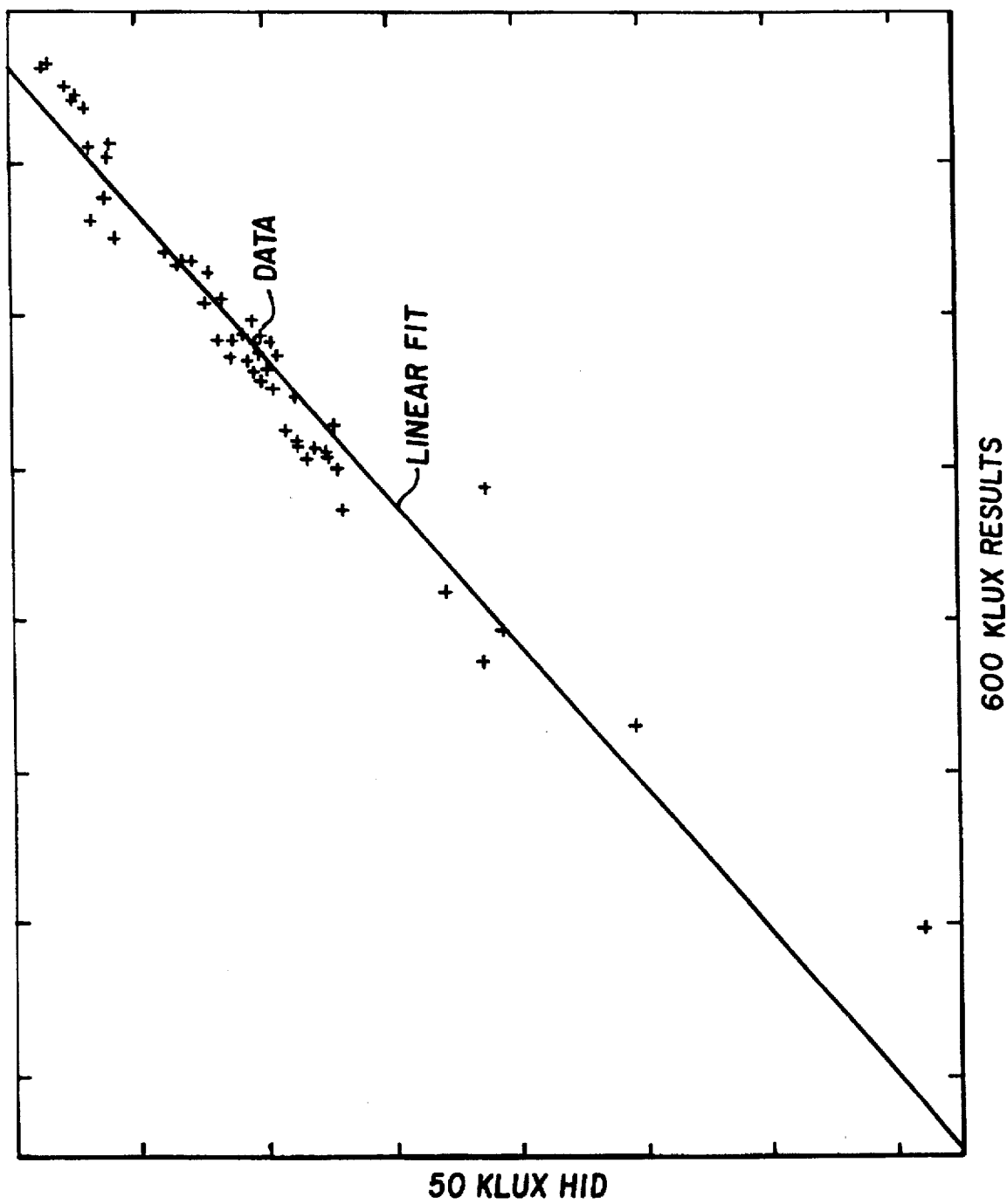
FIG. 5 is a graph illustrating a comparison of high intensity fade data between the apparatus of the invention providing 600K lux of light with a prior art apparatus providing 50K lux. The results correlate very well.

The invention device was compared with samples faded by conventional long-term fade over a three-week period. It was considered that if the long-term fade results over three weeks compared with the rapid fade of the invention device exposed at 600,000 Lux of light were the same, then long-term fade prediction also would be the same. The device of the invention exposing at 600K lux was operated on the samples for 2 days. The prior device operating at 50K lux over three weeks was compared. As shown in FIG. 5, there is a fit of the delta densities.

This test was performed in the following manner: Samples treated by the invention device were compared with samples treated by a conventional long-term fade unit. It was considered that if there was a strong correlation between fade results for the two units then results obtained with the invention device would be predictive of long-term fade tests.

The device of the invention exposing at 600K lux was operated on the samples for 2 days, while the conventional fade unit operated at 50K lux for 3 weeks.

FIG. 5 compares fade results produced by the two units for a number of different color paper test samples. For each sample, its optical density was measured before and after testing and the resulting delta densities are plotted in FIG. 5. As seen in the figure, there is a high degree of correlation (0.97) between the delta densities produced by the conventional and invention device fade.

While the above discussion presumes that photographic samples are being tested, the invention device also would find use in the testing of fade on paint samples and fabric samples. Samples of plastics, such as used in siding and curtains, also could be tested with the invention apparatus. To simulate fade of samples intended for exterior use, the UV and IR light would not be removed in order to better mimic the sun's rays. Samples of clothing often worn inside and for interior paints could utilize light substantially as utilized for photographs. Generally, photographic fading is conducted under conditions of interior light. It is known that window glass filters out UV rays; therefore, interior fade test does not consider the UV exposure fade as pertinent. The device also could be utilized to determine the fade characteristics of materials such as those incorporated in glasses to photochromically change upon being worn in high intensity light areas. These and other uses are apparent to those skilled in the art.

The invention has been described in detail with particular reference to preferred embodiments thereof, but it will be understood that variations and modifications can be effected within the spirit and scope of the invention.

We claim:

1. Apparatus for light fastness testing comprising a light source, means for dividing visible light from ultraviolet and infrared radiation, means to direct the visible component of light into a spherical cavity, and means to mount test samples in apertures in the wall in said cavity.

2. The apparatus of claim 1 wherein said cavity is white.

3. The apparatus of claim 1 wherein said cavity is between about 5 and 15 inches in diameter.

4. The apparatus of claim 1 further comprising air circulation means.

5. The apparatus of claim 2 wherein said light source is at least of 500-watt power.

6. The apparatus of claim 1 wherein test samples placed in said apertures have greater than 500K lux of light applied to them.

7. The apparatus of claim 6 wherein between about 500,000 and 600,000 Lux are applied to said samples.

8. The apparatus of claim 1 wherein the material forming said sphere comprises a thermoplastic resin.

9. The apparatus of claim 5 wherein said light source is a collimated light source.

10. The apparatus of claim 1 wherein said spherical cavity has four apertures for mounting test samples.

11. The apparatus of claim 1 further comprising a heat sink for absorbing the ultraviolet and infrared radiation.

12. The apparatus of claim 9 wherein said means for dividing visible light comprises a cold mirror and a heat absorber.

13. A method of light fading comprising providing apparatus for light fastness testing comprising a light source, means for dividing visible light from ultraviolet and infrared rays, means to direct the visible component of light into spherical cavity, and means to mount test samples in apertures in the wall of in said cavity, placing test samples in said apertures, and subjecting said samples to light levels of greater than 500K lux.

14. The method of claim 13 wherein 10 to 20 days of light exposure are carried out that then allow prediction of 20-year color paper fade.

15. The method of claim 13 wherein said cavity is white.

16. The method of claim 13 wherein said cavity is between about 5 and 15 inches in diameter.

17. The method of claim 13 further comprising air circulation means.

18. The method of claim 13 wherein said light source is at least of 500-watt power.

19. The method of claim 18 wherein test samples placed in said apertures have greater than 500K lux of light applied to them.

20. The method of claim 19 wherein between about 500,000 and 600,000 Lux are applied to said samples.

21. The method of claim 13 wherein the material forming said sphere comprises a polymer.

22. The method of claim 13 wherein said light source is a collimated light source.

23. The method of claim 13 wherein said spherical cavity has four apertures for mounting test samples.

24. The method of claim 13 further comprising a heat sink for absorbing the infrared and ultraviolet radiation.

* * * * *